(12) United States Patent
Peterson

(10) Patent No.: US 8,694,122 B2
(45) Date of Patent: Apr. 8, 2014

(54) SYMMETRICAL OUTPUT NEUROSTIMULATION DEVICE

(75) Inventor: David K. L. Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 754 days.

(21) Appl. No.: 12/821,043

(22) Filed: Jun. 22, 2010

(65) Prior Publication Data

US 2010/0331923 A1  Dec. 30, 2010

Related U.S. Application Data

(60) Provisional application No. 61/220,131, filed on Jun. 24, 2009.

(51) Int. Cl.
*A61N 1/36* (2006.01)

(52) U.S. Cl.
USPC .......................................................... 607/72

(58) Field of Classification Search
USPC ................................................. 607/115–118
See application file for complete search history.

(56) References Cited

U.S. PATENT DOCUMENTS

| | | | |
|---|---|---|---|
| 6,516,227 B1 | 2/2003 | Meadows et al. | |
| 6,895,280 B2 | 5/2005 | Meadows et al. | |
| 6,988,006 B2 * | 1/2006 | King et al. | 607/70 |
| 6,993,384 B2 | 1/2006 | Bradley et al. | |
| 7,539,538 B2 | 5/2009 | Parramon et al. | |
| 8,219,196 B2 * | 7/2012 | Torgerson | 607/27 |
| 2003/0139781 A1 | 7/2003 | Bradley et al. | |
| 2005/0267546 A1 | 12/2005 | Parramon et al. | |
| 2008/0071325 A1 * | 3/2008 | Bradley | 607/48 |

* cited by examiner

*Primary Examiner* — Kennedy Schaetzle
*Assistant Examiner* — Erica Lee
(74) *Attorney, Agent, or Firm* — Vista IP Law Group LLP

(57) ABSTRACT

A method and system of providing therapy to a patient using electrodes implanted adjacent tissue. The method comprises regulating a first voltage at an anode of the electrodes relative to the tissue, regulating a second voltage at a cathode of the electrodes relative to the tissue, and conveying electrical stimulation energy between the anode at the first voltage and the cathode at the second voltage, thereby stimulating the neural tissue. The system comprises a grounding electrode configured for being placed in contact with the tissue, electrical terminals configured for being respectively coupled to the electrodes, a first regulator configured for being electrically coupled between an anode of the electrodes and the grounding electrode, a second regulator configured for being electrically coupled between an anode of the electrodes and the grounding electrode, and control circuitry configured for controlling the regulators to convey electrical stimulation energy between the anode and cathode.

7 Claims, 8 Drawing Sheets

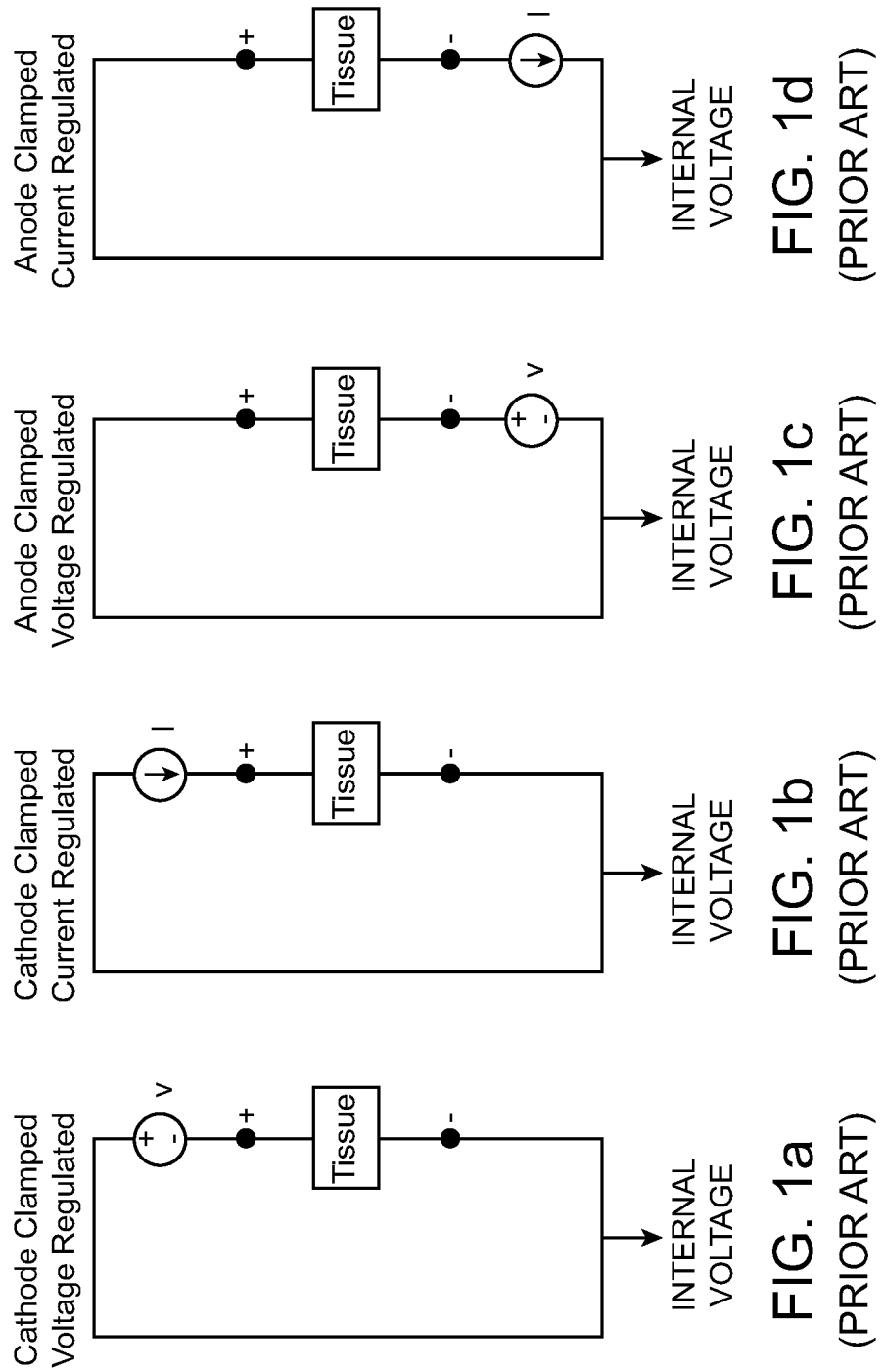

SYMMETRICAL OUTPUT NEUROSTIMULATION DEVICE

RELATED APPLICATION

The present application claims the benefit under 35 U.S.C. §119 to U.S. provisional patent application Ser. No. 61/220,131, filed Jun. 24, 2009. The foregoing application is hereby incorporated by reference into the present application in its entirety.

FIELD OF THE INVENTION

The present invention relates to tissue stimulation systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes an electrode lead implanted at the desired stimulation site and an implantable pulse generator (IPG) implanted remotely from the stimulation site, but coupled either directly to the electrode lead or indirectly to the electrode lead via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, rate, and burst rate of the stimulation pulses.

The neurostimulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

Electrical stimulation energy may be delivered from the neurostimulator to the electrodes using one or more current-controlled sources for providing stimulation pulses of a specified and known current (i.e., current regulated output pulses), or one or more voltage-controlled sources for providing stimulation pulses of a specified and known voltage (i.e., voltage regulated output pulses). The circuitry of the neurostimulator may also include voltage converters, power regulators, output coupling capacitors, and other elements as needed to produce constant voltage or constant current stimulus pulses. Conventional battery-operated neurostimulators typically apply stimulation pulses to the tissue that are referenced to an internal circuit voltage in the neurostimulator, with a relatively low impedance connection being located between one or more stimulation electrodes and internal circuitry. This relatively low impedance effectively clamps the voltage on these stimulation electrodes to the internal circuit voltage.

For example, a voltage source can be coupled between the internal circuitry and an anode to create a cathode clamped voltage regulated circuit (FIG. 1a), a current source can be coupled between the internal circuitry and an anode to create a cathode clamped current regulated circuit (FIG. 1b), a voltage source can be coupled between the internal circuitry and a cathode to create an anode clamped voltage regulated circuit (FIG. 1c), and a current source can be coupled between the internal circuitry and a cathode to create an anode clamped current regulated circuit (FIG. 1d). It can be appreciated that the reference voltage will be at the cathodes for the topologies illustrated in FIGS. 1a and 1b and will be at the anodes for the topologies illustrated in FIGS. 1c and 1d.

Because the voltage at the unregulated side of the electrode will be clamped to the voltage of the internal circuitry, and because the stimulation output circuitry may be unbalanced in that some components in the circuitry (coupling capacitors, protection circuits, etc.) may be present on the cathode side of the circuit but not the anode side of the circuit, or vice versa, the output stimulation circuitry between the cathode and the anode will be asymmetrical, such that the cathode and the anode will be asymmetrically referenced to the internal circuit. For example, a shift in voltage in the output stimulation circuit results in asymmetrical voltage shifts between the anodes and cathodes.

In particular, the voltage of the common mode signal (i.e., the average of the anode voltage shift and cathode voltage shift relative to the reference voltage) will be equal to or greater than the differential voltage between the cathode and anode. For example, as shown in FIG. 2a, when the cathode voltage is at the internal reference voltage, the common mode signal is equal to one-half the differential voltage between the cathode and anode. As shown in FIG. 2b, when the cathode voltage is above the internal reference voltage, the voltage of the common mode signal is greater than one-half the differential voltage between the cathode and anode. As shown in FIG. 2c, when the cathode voltage is below the internal reference voltage, the voltage of the common mode signal is likewise greater than one-half the differential voltage between the cathode and anode. The asymmetry between anodes and cathodes in the output stimulation circuitry may be associated with undesired side effects during stimulation that lead to reduced patient comfort. In particular, parasitic coupling of the common mode signal to the implantable device can give rise to an additional stimulation signal that is superimposed on the differential stimulation signal. Even if the common mode signal is subthreshold by itself, it can modulate the differential stimulation signal, causing unwanted activation of neural tissue.

In addition to the problem of asymmetry in the output stimulation circuit, referencing the voltage at the cathodes and anodes to an internal circuit may require excessive voltage levels at the cathodes and anodes in order to maintain the desired voltage potential therebetween. For example, if the desired voltage potential between a cathode and an anode is 5V, and if the internal voltage is 20V, the voltage at the anode would have to be 25V and the voltage at the cathode would have to be 20V. The increased voltage at the electrodes will increase the voltage relative to the tissue, which may cause problems such as unwanted stimulation and even electrochemical reactions resulting in corrosion of the electrodes.

There, thus, remains a need for an improved method and system for conveying stimulation to tissue in a controlled manner.

SUMMARY OF THE INVENTION

In accordance with a first aspect of the present inventions, a method of providing therapy to a patient using an array of electrodes implanted adjacent neural tissue (e.g., spinal cord tissue) of the patient is provided. The method comprises regulating a first voltage at an anode of the electrodes relative to the neural tissue, regulating a second voltage at a cathode of the electrodes relative to the tissue, and conveying electrical stimulation energy between the anode at the first voltage and the cathode at the second voltage, thereby stimulating the neural tissue. In one method, the voltages on the anode and cathode are regulated in a balanced fashion, such that an average shift in voltage on the anode and cathode relative to the neural tissue is equal to or less than one half a differential voltage between the anode and cathode. Optimally, the voltage shifts at the anode and cathode relative to the neural tissue may be equal in magnitude, but opposite in polarity (i.e., anode voltage shifts up and cathode voltage shifts down by the amount). An optional method comprises regulating a first current flowing through the anode, and regulating a second current flowing through the cathode. Furthermore, the values for the first current and the second current necessary to achieve the first and second voltages may be computed.

In accordance with a second aspect of the present inventions, a neurostimulation system is provided. The neurostimulation system comprises a grounding electrode configured for being placed in contact with neural tissue, and a plurality of electrical terminals configured for being respectively coupled to an array of electrodes. The neurostimulation system further comprises a first regulator configured for being electrically coupled between an anode of the electrodes and the grounding electrode, a second regulator configured for being electrically coupled between an anode of the electrodes and the grounding electrode, and control circuitry configured for controlling the first and second regulators to convey electrical stimulation energy between the anode and the cathode.

In one embodiment, each of the first and second regulators comprises a voltage source. In another embodiment, each of the first and second regulators comprises a current source. In the latter case, the control circuitry is configured for controlling the current sources to output the same current value and/or the control circuitry may be further configured for determining values for the first current and the second current necessary to achieve the first and second voltages. In another embodiment, the control circuitry may be configured for controlling the regulators such that an average shift in voltage on the anode and cathode relative to the neural tissue is equal to or less than one half a differential voltage between the anode and cathode. Optimally, the voltage shifts at the anode and cathode relative to the neural tissue may be equal in magnitude, but opposite in polarity (i.e., anode voltage shifts up and cathode voltage shifts down by the amount). The neurostimulation system may comprise a housing containing the plurality of electrical terminals, first and second voltage regulators, and control circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 1a-1d are prior art circuit diagrams of different prior art tissue stimulation topologies;

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 2A:
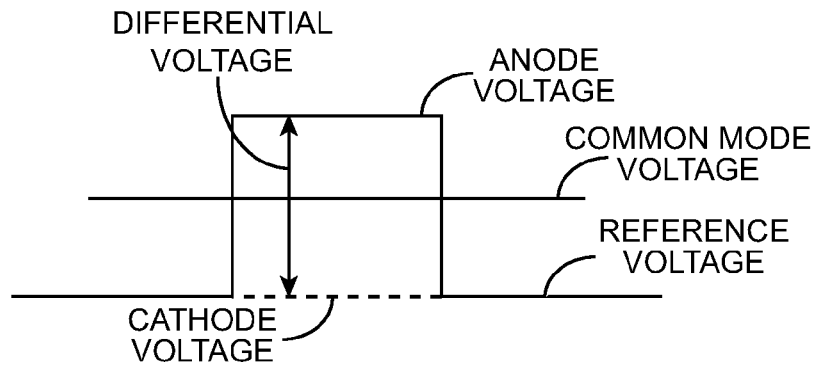
FIGS. 2a-2c are prior art diagrams of a cathode voltage and an anode voltage generated by the tissue stimulation topologies of FIGS. 1a-1d.
Figure 2B:
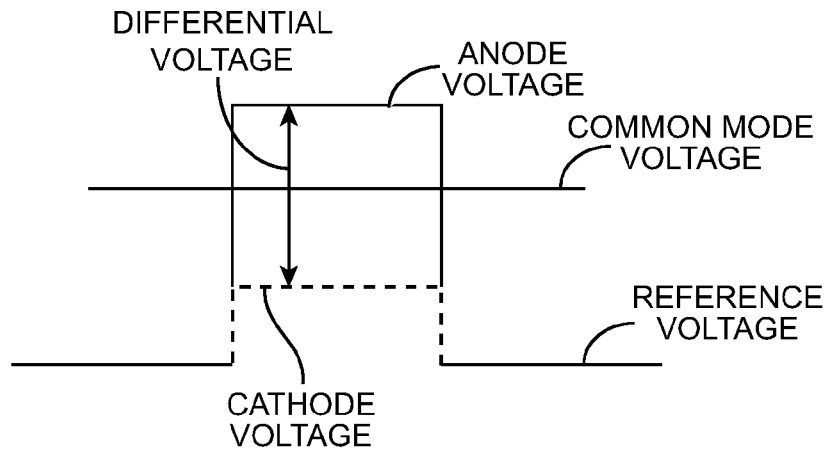
Figure 2C:
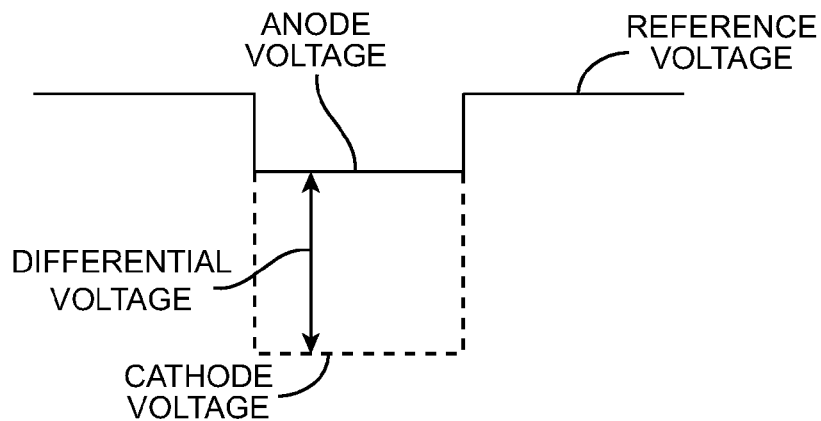
Figure 3:
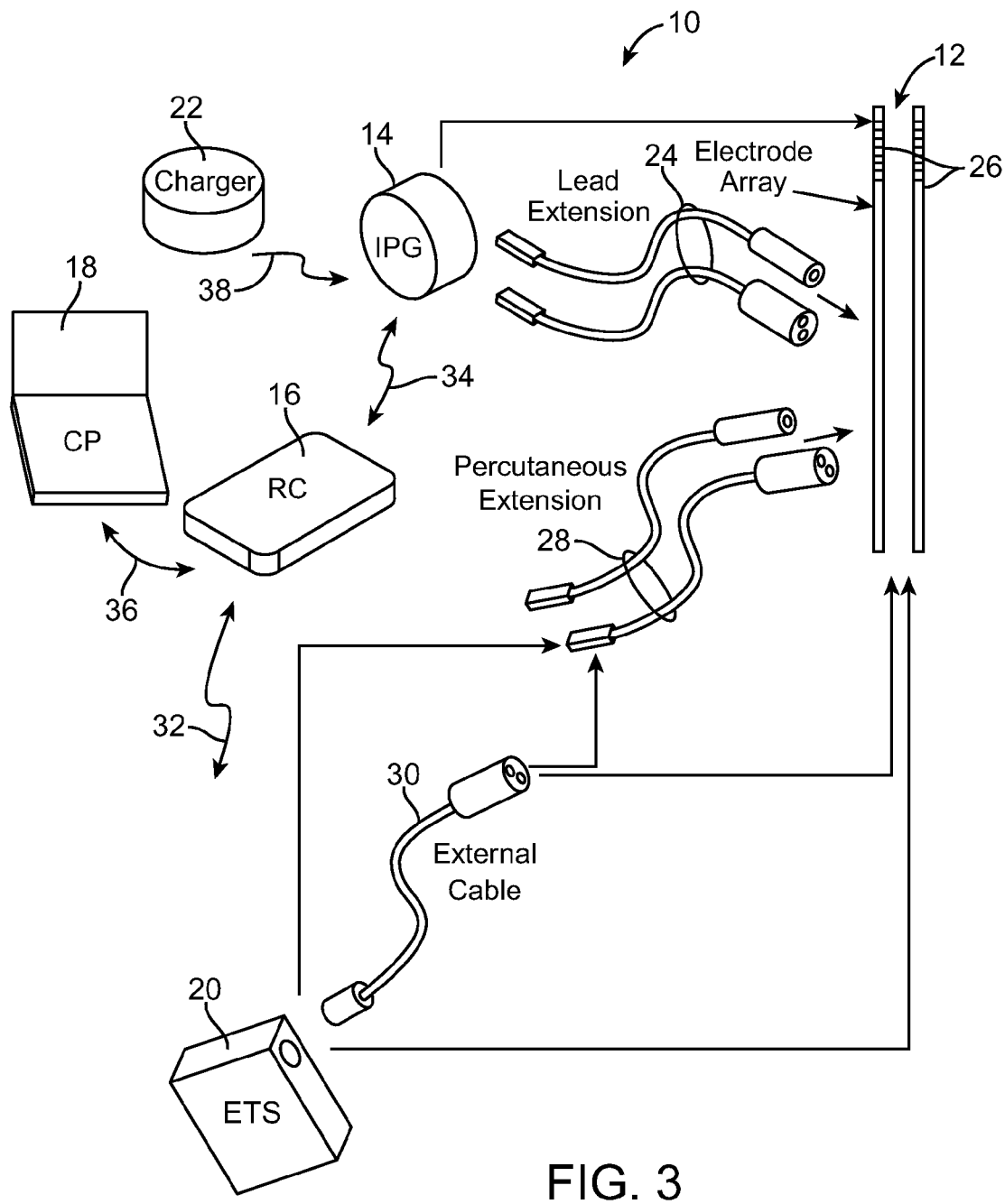
FIG. 3 is plan view of one embodiment of a spinal cord stimulation (SCS) system arranged in accordance with the present inventions.

Turning first to FIG. 3, an exemplary spinal cord stimulation (SCS) system 10 generally includes one or more (in this case, two) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 4:
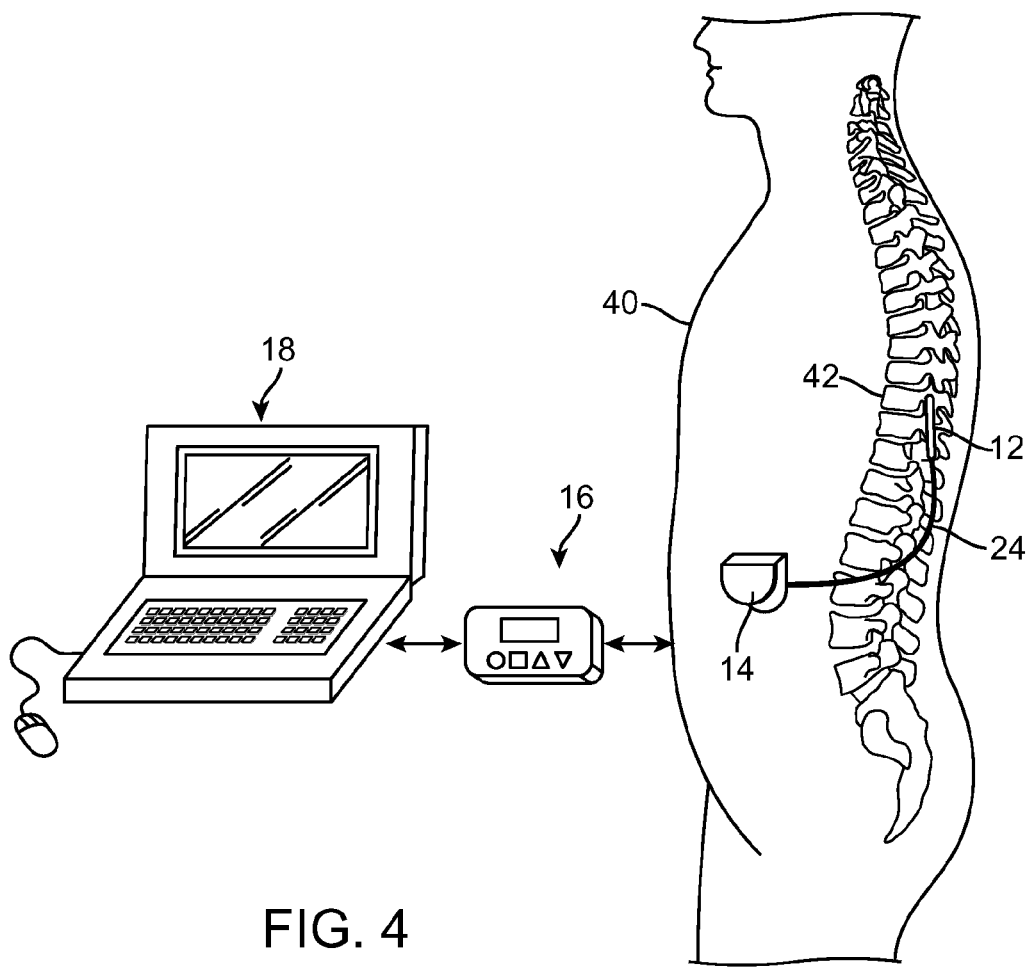
FIG. 4 is a plan view of the SCS system of FIG. 3 in use with a patient.

As shown in FIG. 4, the electrode leads 12 are implanted within the spinal column 42 of a patient 40. The preferred placement of the electrode leads 12 is adjacent, i.e., resting upon near, or upon the dura, adjacent to the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

Figure 5:
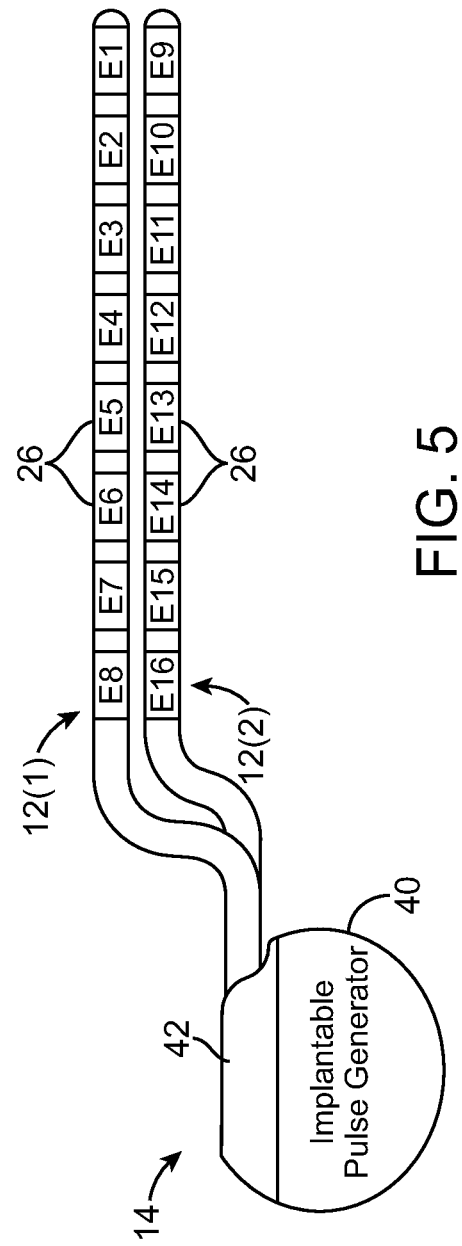
FIG. 5 is a profile view of an implantable pulse generator (IPG) used in the SCS system of FIG. 3.

Referring now to FIG. 5, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 50 for housing the electronic and other components (described in further detail below), and a connector 52 to which the proximal ends of the stimulation leads 12 mate in a manner that electrically couples the electrodes 26 to the internal electronics (described in further detail below) within the outer case 50. The outer case 50 is composed of an electrically conductive, biocompatible material, such as titanium, and forms a hermetically sealed compartment wherein the internal electronics are protected from the body tissue and fluids. In some cases, the outer case 50 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

Electrical stimulation will occur between two (or more) activated electrodes, one of which may be the IPG case 50. Simulation energy may be transmitted to the tissue in a monopolar or multipolar (e.g., bipolar, tripolar, etc.) fashion. Monopolar stimulation occurs when a selected one of the lead electrodes 26 is activated along with the case 50 of the IPG 14, so that stimulation energy is transmitted between the selected electrode 26 and case 50. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 6:
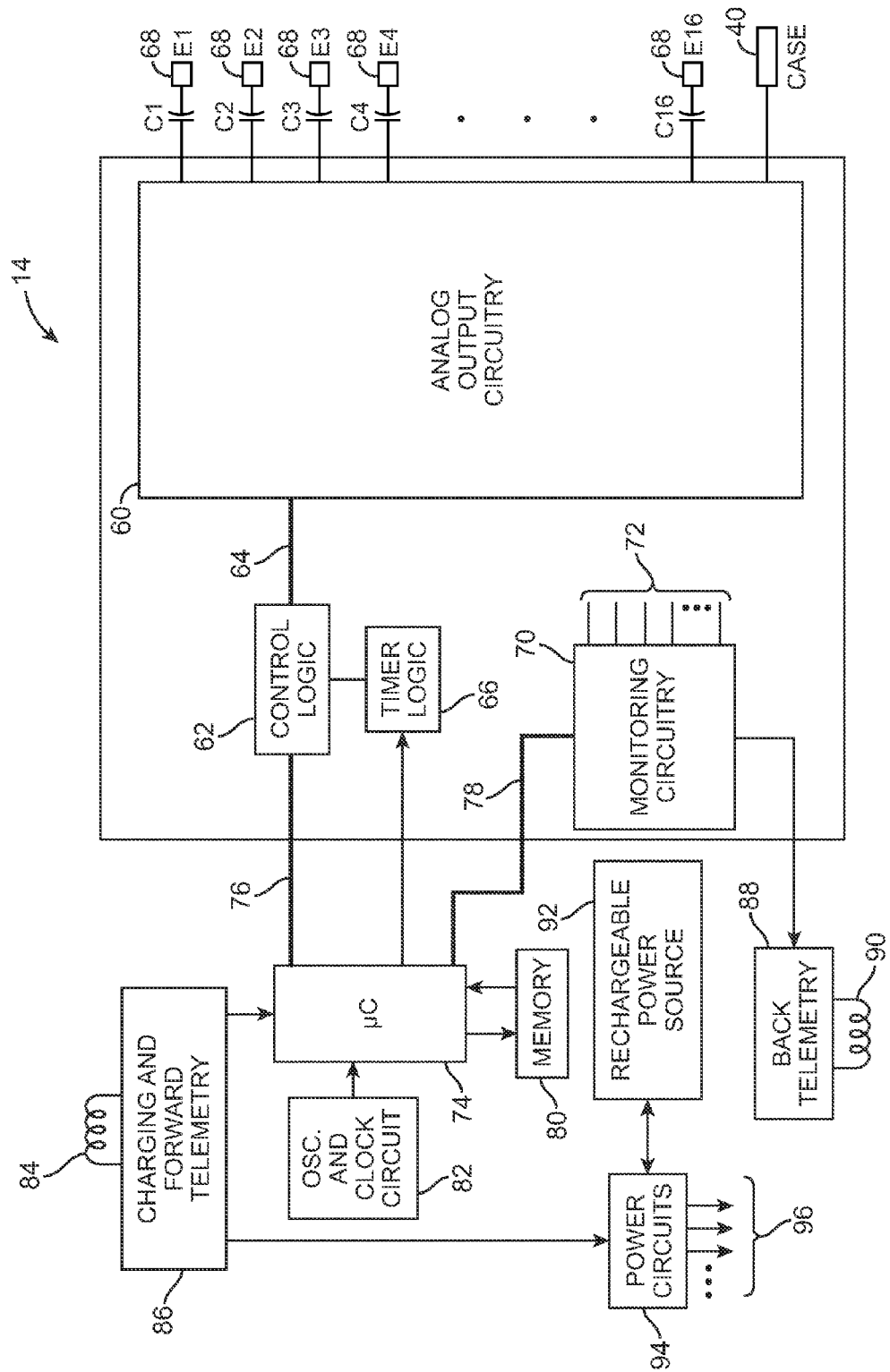
FIG. 6 is a block diagram of the internal components of the IPG of FIG. 5.

Turning next to FIG. 6, the main internal components of the IPG 14 will now be described. The IPG 14 includes analog output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The electrical stimulation energy generated by the output analog circuitry 60 is output via capacitors C1-C16 to electrical terminals 68 corresponding to the electrodes 26.

The analog output circuitry 60 may either comprise independently controlled current sources for providing electrical stimulation energy of a specified and known amperage to or from the electrical terminals 68, or independently controlled voltage sources for providing electrical stimulation energy of a specified and known voltage at the electrical terminals 68 or to multiplexed current or voltage sources that are then connected to the electrical terminals 68. The operation of the analog output circuitry 60, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

Significantly, as will be described in further detail below, the analog output circuitry 60 presents symmetrical outputs to both the anodes and cathodes that will not be subject to the differential voltage shifts in the circuitry discussed in the background. Furthermore, the analog output circuitry 60 references the voltages at the anodes and cathodes to the tissue rather than a voltage internal to the IPG 14.

The IPG 14 further comprises monitoring circuitry 70 for monitoring the status of various nodes or other points 72 throughout the IPG 14, e.g., power supply voltages, temperature, battery voltage, and the like. The monitoring circuitry 70 is also configured for measuring electrical parameter data (e.g., electrode impedance and/or electrode field potential). The IPG 14 further comprises processing circuitry in the form of a microcontroller (μC) 74 that controls the control logic 62 over data bus 76, and obtains status data from the monitoring circuitry 70 via data bus 78. The IPG 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and stimulation parameters. In controlling the operation of the IPG 14, the microcontroller 74 is able to individually generate stimulus pulses at the electrical terminals 68 using the analog output circuitry 60, in combination with the control logic 62 and timer logic circuitry 66, thereby allowing each electrical terminal 68 (and thus, each electrode 26) to be paired or grouped with other electrical terminals 68 (and thus, other electrodes 26), including the monopolar case electrode, to control the polarity, amplitude, rate, pulse width, pulse shape, burst rate, and channel through which the current stimulus pulses are provided. The microcontroller 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the receiving coil 84.

To recharge the power source 92, the external charger 22 (shown in FIG. 3), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation energy in accordance with the control signals.

As briefly discussed above, the analog output circuitry 60 presents symmetrical outputs to both the anodes and cathodes. For example, with reference to FIG. 7a, a first voltage source 102a is coupled to an anode 100a, and a second voltage source 102b is coupled to a cathode 100b. This is in contrast to the single-ended voltage regulated circuit illustrated in FIG. 1a. Thus, because there is a voltage source at both the anode 100a and the cathode 100b, voltage shifts within the analog output circuitry 60 will not be conducted to the anode 100a and cathode 100b differentially. Alternatively, with reference to FIG. 7b, a first current source 104a is coupled to the anode 100a, and a second current source 104b is coupled to the cathode 100b. This is in contrast to the single-ended current regulated circuit illustrated in FIG. 1b. In this case, the current sources present a high impedance to the respective anode 100a and cathode 100b, thereby isolating the anode 100a and cathode 100b from voltage shifts within the analog output circuitry 60.

Figure 10:
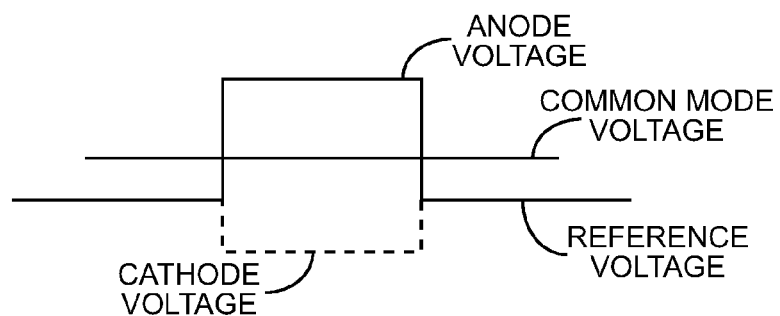
FIG. 10 is a diagram of a cathode voltage and an anode voltage generated by the tissue stimulation topologies of FIGS. 1a-1d.

As also briefly discussed above, the analog output circuitry 60 references the voltages at the anodes and cathodes to the tissue rather than a voltage internal to the IPG 14. To this end, the IPG 14 is provided with a grounding electrode 106 configured for being placed in contract with tissue. For example, the grounding electrode 106 may be located on the case 50 or may be the case 50 itself. In the illustrated embodiment, the analog output circuitry 60 regulates the voltages at the anodes and cathodes, such that the common mode signal (i.e., the average of the anode voltage shift and cathode voltage shift relative to the reference voltage (in this case, the grounding electrode 106)) will be equal to or less than the differential voltage between the cathodes and anodes, as illustrated in FIG. 10.

With reference back to FIG. 7a, the first voltage source 102a is electrically coupled between the anode 100a and the grounding electrode 106, and the second voltage source 102b is electrically coupled between the cathode 100b and the grounding electrode 106. As a result, the voltages at the respective anode 100a and cathode 100b relative to the tissue may be controlled, so that large voltages are not applied to the tissue. The voltage values respectively output by the first and second voltage sources 102a, 102b can be set to be equal in order to minimize the maximum voltage seen by the tissue. For example, if the desired voltage potential between the anode 100a and the cathode 100b is 5V, the first voltage source 102a can be set to output a voltage of 2.5V relative to the grounding electrode 106 (and thus, the tissue), and the second voltage source 102b can be set to output a voltage of −2.5V relative to the grounding electrode 106 (and thus, the tissue). Essentially, in this case, the voltage of the common mode signal would be zero. Notably, the internal reference voltage of the analog output circuitry 60 is irrelevant, since the voltage sources 102a, 102b are not referenced to this internal voltage.

Figure 7A:
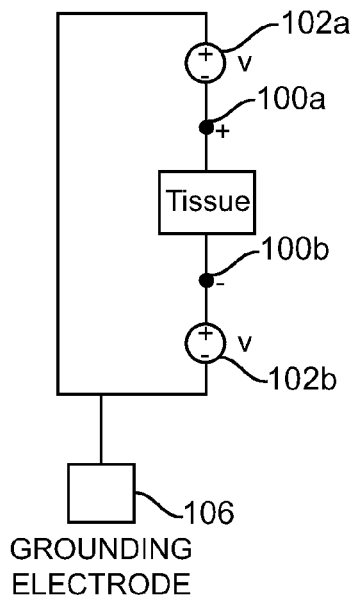
FIGS. 7a and 7b are circuit diagrams of two tissue stimulation topologies used by the SCS system of FIG. 3.
Figure 7B:
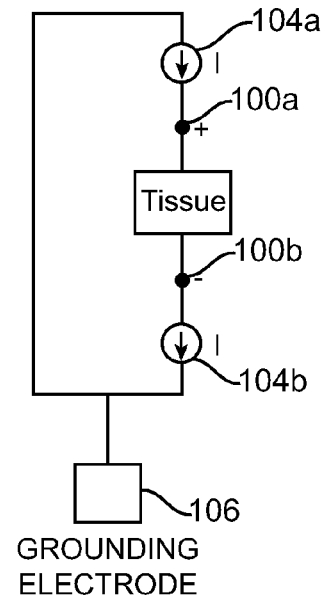

With reference to FIG. 7b, the first current source 104a is electrically coupled between the anode 100a and the grounding electrode 106, and the second current source 104b is electrically coupled between the cathode 100b and the grounding electrode 106. Thus, the electrical current flowing through each of the anode 100a and the cathode 100b can be controlled. In this case, where there the anode 100a and cathode 100b are the only active electrodes, the absolute value of the electrical current magnitude flowing through the anode 100a will be essentially equal to the electrical current magnitude flowing through the cathode 100b; however, the electrical currents flowing through the anode 100a and cathode 100b will be oppositely polarized. For example, the current output by the first current source 104a may be set at 2.5 mA, while the current output by the second current source 104b may be set at −2.5 mA. Essentially, in this case, the voltage of the common mode signal would be zero assuming that the tissue impedances on the cathodes and anodes are equal.

Although the current sources 104a, 104b regulate the current flowing through the anode 100a and cathode 100b, the voltages at the respective anode 100a and cathode 100b relative to the tissue may still be controlled, so that large voltages are not applied to the tissue. In particular, the currents required to be output by the respective current sources 100a, 100b to achieve the voltage distribution desired at the respective anode 100a and cathode 100b relative to the tissue can be computed in a conventional manner.

Figure 8A:
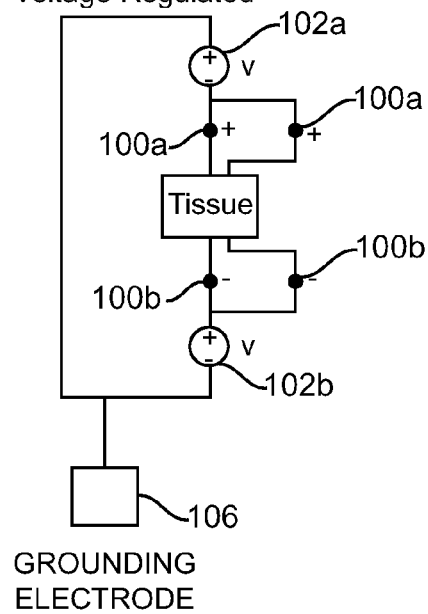
FIGS. 8a and 8b are circuit diagrams of two alternative tissue stimulation topologies used by the SCS system of FIG. 3.
Figure 8B:
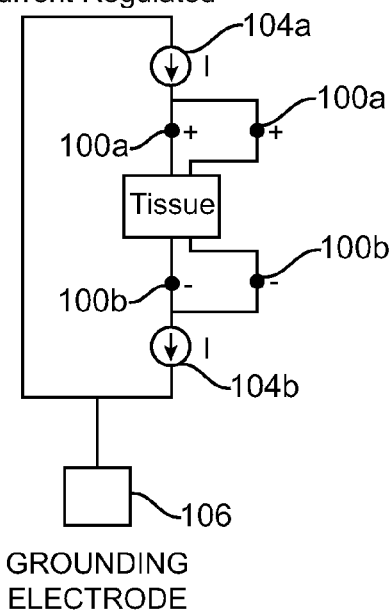
Figure 9A:
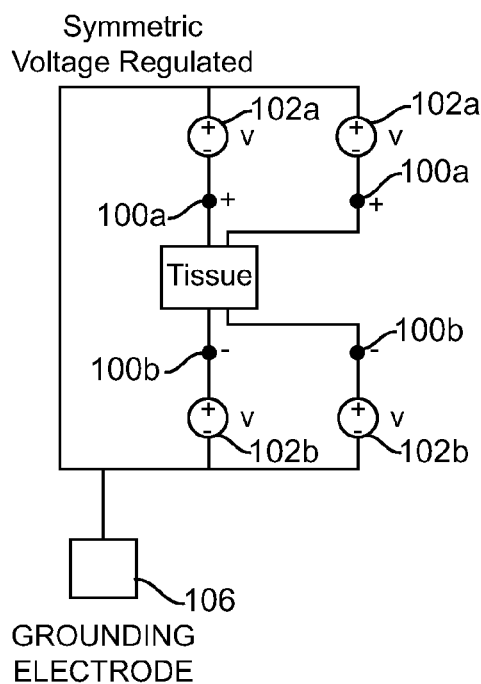
FIGS. 9a and 9b are circuit diagrams of two alternative tissue stimulation topologies used by the SCS system of FIG. 3.
Figure 9B:
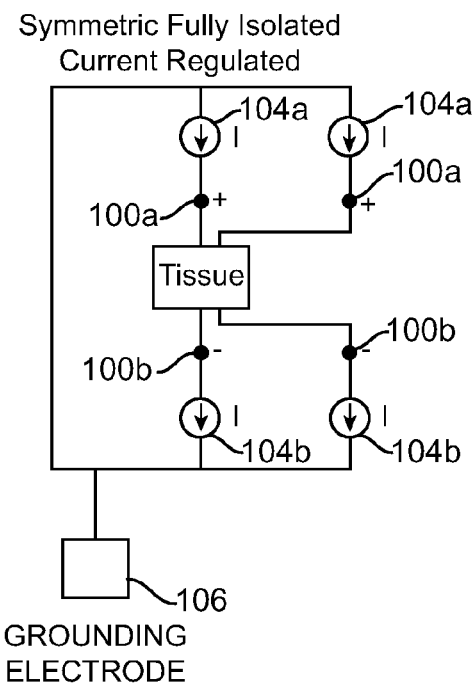

Although each of the voltage sources 102a, 102b and current sources 104a, 104b in the topologies illustrated in FIGS. 7a and 7b are coupled to only a single electrode, it should be appreciated that each of these sources can be coupled to multiple electrodes (either a group of anodes 100a or a group of cathodes 100b), as illustrated in FIGS. 8a and 8b. Furthermore, multiple sources of the same type can be respectively connected to multiple electrodes at the same time. For example, two voltage sources 102a or two current sources 104a can be respectively connected to two anodes 100a at the same time, or two voltage sources 102b or two current sources 104b can be respectively connected to two cathodes 100 at the same time, as illustrated in FIGS. 9a and 9b. Thus, this concept can be applied to a multiplicity of anodes and a multiplicity of cathodes where the positive shifts in voltage on the anode and negative shifts in voltage on the cathodes are such that the average shift is zero or at least less than one half of the maximum differential voltage between any anode and cathode pair during the stimulation pulse.

It can be appreciated from the foregoing that the voltage or voltages at the anode or anodes 100a relative to the tissue can be regulated, and the voltage or voltages at the cathode or cathodes 100b can be regulated, while the electrical stimulation energy is conveyed between the anode or anodes 100a and the cathode or cathodes 100b. If any of the topologies illustrated in FIG. 7b, 8b, or 9b are used, the currents flowing through the anode or anodes 100a and the cathode or cathodes 100b can be regulated.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system, comprising:
a grounding electrode configured for being placed in contact with neural tissue;
a plurality of electrical terminals configured for being respectively coupled to an array of electrodes;
a first regulator configured for being electrically coupled between an anode of the electrodes and the grounding electrode;
a second regulator configured for being electrically coupled between a cathode of the electrodes and the grounding electrode; and
control circuitry configured for controlling the first and second regulators to convey electrical stimulation energy between the anode and the cathode, such that an average shift in voltage on the anode and cathode relative to the grounding electrode is equal to or less than one half a differential voltage between the anode and cathode.

2. The neurostimulation system of claim 1, wherein each of the first and second regulators comprises a voltage source.

3. The neurostimulation system of claim 1, wherein each of the first and second regulators comprises a current source.

4. The neurostimulation system of claim 3, wherein the control circuitry is further configured for controlling the first regulator to regulate a first voltage of the anode relative to the grounding electrode, regulate a second voltage at the cathode relative to the grounding electrode, regulate a first current flowing through the anode, regulate a second current flowing through the cathode, and determining values for the first current and the second current necessary to achieve the first and second voltages.

5. The neurostimulation system of claim 1, wherein the control circuitry is further configured for controlling the first regulator to regulate a first voltage at the anode relative to the grounding electrode, regulate a second voltage at the cathode relative to the grounding electrode, and controlling the regulators to shift the voltage on the anode upward relative to the grounding electrode the same amount as the voltage on the cathode shifts downward relative to the grounding electrode.

6. The neurostimulation system of claim 1, further comprising the array of electrodes.

7. The neurostimulation system of claim 1, further comprising a housing containing the plurality of electrical terminals, first and second regulators, and control circuitry.

* * * * *